(12) United States Patent
Bodepudi et al.

(10) Patent No.: US 7,138,504 B2
(45) Date of Patent: Nov. 21, 2006

(54) REAGENTS AND METHODS FOR MYCOPHENOLIC ACID IMMUNOASSAY

(75) Inventors: Vani B. Bodepudi, San Ramon, CA (US); Amy P. Tsai, San Jose, CA (US); Weixing Luo, Fremont, CA (US); Rueyming Loor, Danville, CA (US)

(73) Assignee: Microgenics Corporation, Fremont, CA (US)

( * ) Notice: Subject to any disclaimer, the term of this patent is extended or adjusted under 35 U.S.C. 154(b) by 0 days.

(21) Appl. No.: 11/201,992

(22) Filed: Aug. 11, 2005

(65) Prior Publication Data

US 2006/0035297 A1    Feb. 16, 2006

Related U.S. Application Data

(60) Provisional application No. 60/601,105, filed on Aug. 12, 2004.

(51) Int. Cl.
*C07K 17/06* (2006.01)
*C07K 16/44* (2006.01)
*C12N 9/96* (2006.01)
*G01N 33/353* (2006.01)
*G01N 33/533* (2006.01)

(52) U.S. Cl. ............... 530/403; 435/7.91; 435/7.92; 435/188; 436/518; 436/544; 436/546; 530/388.9; 530/389.8; 530/406

(58) Field of Classification Search .......... 530/388.9, 530/403, 406, 389.8; 435/7.91, 188, 7.92; 436/518, 544, 546
See application file for complete search history.

(56) References Cited

U.S. PATENT DOCUMENTS

| 4,444,887 A | 4/1984 | Hoffmann |
| 4,472,500 A | 9/1984 | Milstein et al. |
| 4,491,632 A | 1/1985 | Wands et al. |
| 4,708,929 A | 11/1987 | Henderson |
| 5,032,503 A | 7/1991 | Khanna et al. |
| 5,120,653 A | 6/1992 | Henderson |
| 5,254,677 A | 10/1993 | Guder et al. |
| 5,444,161 A | 8/1995 | Manning et al. |
| 5,514,560 A | 5/1996 | Manning et al. |
| 5,604,091 A | 2/1997 | Henderson |
| 5,643,734 A | 7/1997 | Henderson |
| 6,225,073 B1 | 5/2001 | Alexander et al. |
| 6,524,808 B1 | 2/2003 | Dorn et al. |

OTHER PUBLICATIONS

Glucuronide and glucoside conjugation of mycophenolic acid by human liver, kidney and intestinal microsomes by M. Shipkova et al; British Journal of Pharmacology (2001); pp. 1027-1034.

*Primary Examiner*—Mary E. Ceperley
(74) *Attorney, Agent, or Firm*—Andrus, Sceales, Starke & Sawall, LLP

(57) ABSTRACT

The invention teaches derivatives of mycophenolic alcohol and methods of preparing immunogens and other conjugates useful in immunoassays for quantitatively measuring concentrations of mycophenolic acid (MPA) and/or active metabolites of MPA in patient specimens. Antibodies produced from the disclosed immunogens capable of binding to MPA with cross-reactivity of no more than 5% with inactive metabolites and commonly co-prescribed drugs. Further, immunoassays for measuring the concentration of MPA using such antibodies are taught.

15 Claims, No Drawings

REAGENTS AND METHODS FOR MYCOPHENOLIC ACID IMMUNOASSAY

CROSS REFERENCE TO RELATED APPLICATION

The present application is based on and claims priority from U.S. Provisional Patent Application Ser. No. 60/601,105 filed on Aug. 12, 2004.

FIELD OF THE INVENTION

The present invention is directed to immunoassays for detecting and/or measuring concentrations of mycophenolic acid and, optionally, its pharmacologically active metabolite, acyl glucuronide, and/or the pro-drug mycophenolate mofetil. The present invention further encompasses reagents useful for performing such immunoassays including, but not limited to, antibodies capable of specifically binding mycophenolic acid and labeled conjugates that bind to or compete with mycophenolic acid.

BACKGROUND OF THE INVENTION

Mycophenolic acid (MPA) is a metabolite of the pro-drug mycophenolate mofetil (MMF, CellCept®), widely used for the prevention of rejection in patients receiving renal, heart, or liver transplants. Chemically, MMF is 2-morpholinoethyl (E)-6-(1,3-dihydro-4-hydroxy-6-methoxy-7-methyl-3-oxo-5-isobenzofuranyl)-4-methyl-4-hexenoate. After administration, MMF is rapidly absorbed and hydrolyzed essentially completely to MPA. Biochemically, MPA is a potent and specific inhibitor of inosine-monophosphate dehydrogenase (IMPDH), an enzyme necessary for de novo purine synthesis used by B- and T-lymphocytes. The inhibition of IMPDH by MPA at the cellular level suppresses proliferation of B- and T-lymphocytes, due to their dependency on de novo purine synthesis and, thus, results in immunosuppression at the organism level. MPA is, at times, co-administered with cyclosporine or tacrolimus in transplant patients to further enhance immunosuppression.

MPA has an acceptable therapeutic window in the range of 1–3.5 mg/L in serum or plasma. Because of its immunosuppressive effects, circulating levels of MPA beyond this range are associated with an increased risk of infections or leukopenia. Therefore, levels of MPA must be monitored to insure effective use of the drug while minimizing the risk of adverse side effects in patients.

MPA is further metabolized by UDP-glucuronosyl transferases primarily to a phenolic glucuronide, 7-O-MPAG, which is pharmacologically inactive. However, a minor metabolite, acyl glucuronide (AcMPAG), has been described to have activity similar to that of MPA with regards to inhibiting IMPDH, possibly contributing to the adverse effects of MPA therapy. See Shipkova et al., *British Journal of Pharmacology* 132:1027–1034 (2001). Therefore, therapeutic drug monitoring in patients receiving MPA is likely improved if levels of the active metabolite, AcMPAG, are also measured as part of the active MPA concentration, while the inactive metabolite, 7-O-MPAG, remains undetectable by the assay.

In developing an immunoassay for the detection of a small molecule target, such as a drug, which often lacks inherent antigenicity, an immunogenic compound must first be made. When the target drug is an immunosuppressant, the challenge to make an immunogenic compound increases. Typically, larger antigenic proteins, polypeptides, or other antigenic biomolecules are conjugated to the drug. Still, the immunogen must be capable of stimulating production of an antibody that interacts specifically with at least a portion of the target drug and not just the conjugated antigenic biomolecule.

Further, detection of a drug in an immunoassay generally requires the use of a detectable component or label including, but not limited to, radioisotopes, enzymes, fluorescent molecules, and particles. The label is typically conjugated to an antibody or antibody fragment, in the case of a sandwich immunoassay, or to the drug or analog of the drug, in the case of a competitive immunoassay.

The chemical structure of MPA is represented by the formula:

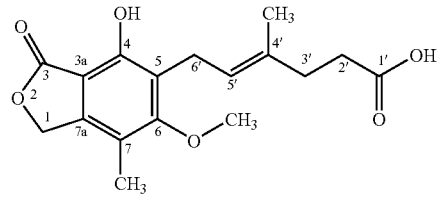

Modifications of MPA, for the purpose of developing immunoassays, have been previously described. U.S. Pat. No. 6,225,073 to Alexander et al., incorporated herein in entirety, teaches compounds comprising MPA bound to a polypeptide by replacement of one or more hydrogen atoms in various functional groups. For example, modifications of MPA at existing functional groups, such as the phenolic hydroxy group at position 4 or the carboxyl group at position 1', are disclosed. Also, the methoxy group at position 6 of the isobenzofuranyl ring system may be cleaved to form a phenolic hydroxy group that is reacted to form an ether linkage. Alternatively, a functional group can be added via oxidation of a C—H bond, for example, the methyl group at position 7 of the isobenzofuranyl ring. Further, Alexander et al. used immunogens prepared by conjugating keyhole limpet hemocyanin (KLH) to MPA via substitution of the hydrogen atom in the phenolic hydroxy group at position 4, or via oxidation of the methyl group at position 7, to produce monoclonal antibodies capable of specifically binding MPA but little or no cross-reactivity to mycophenolic acid glucuronide (MPAG).

U.S. Pat. No. 6,524,808 to Dorn et al., incorporated herein in entirety, discloses conjugates made via attachment of ligands to MPA at a carbon atom in the hexanoic chain. Such conjugates were used for the purposes of making enzyme conjugates for a homogeneous enzyme inhibition immunoassay, not for immunogenic conjugates.

SUMMARY OF THE INVENTION

The conjugates of the present invention were prepared using mycophenolic alcohol (MPAlc) instead of MPA. An immunogenic conjugate of MPAlc was used to produce antibodies with appropriate sensitivity and specificity for use in immunoassays for detecting MPA. Other conjugates are disclosed, such as labeled conjugates used for detection purposes. The conjugates are useful as reagents for developing and performing immunoassays to detect MPA. Such immunoassays include enzyme-linked immunoassays (ELISA), fluorescence polarization immunoassays (FPIA), immunoturbidimetric assays, and cloned enzyme-donor immunoassays (CEDIA), among others.

In particular, CEDIA® (a registered trademark of Roche Diagnostics) has proven to be a highly accurate method for quantitation of therapeutic drugs and drugs of abuse. CEDIA is the subject of several patents including U.S. Pat. No. 4,708,929 (incorporated in entirety herein) which claims competitive homogeneous assay methods, U.S. Pat. No. 5,120,653 (incorporated in entirety herein) claiming a recombinant DNA sequence for coding the enzyme donor fragment and a host for such a vector, U.S. Pat. No. 5,604,091 (incorporated in entirety herein) which claims amino acid sequences of the enzyme donor fragment, and U.S. Pat. No. 5,643,734 (incorporated in entirety herein) which teaches and claims kits for CEDIA assays.

DETAILED DESCRIPTION OF THE INVENTION

The present invention, in all of its interrelated embodiments, is focused on the preparation of derivative analogs of MPAlc which can then be used to form immunogens by coupling the derivatives to immunogenic polypeptides or other antigenic carrier materials and subsequently used to obtain antibodies specific for MPA or MPA and AcMPAG. Additionally, the derivatives of MPAlc can be used to form enzyme, enzyme donor, or labeled conjugates which are useful as detection reagents in immunoassays for MPA.

In one embodiment of the present invention, MPA is converted to MPAlc, by replacement of the carboxyl group at position 1' with a hydroxy moiety as described in Example 1, and then further modified to form a MPAlc-carb-NHS ester via linking from the hydroxyl oxygen, as described in Example 2. The ester can be used to form an immunogen by conjugation to an immunogenic molecule including, but not limited to, keyhole limpet hemocyanin (KLH), bovine serum albumin (BSA), and ovalbumin, as further described in Example 2.

In another aspect of the invention, the resulting immunogenic conjugate of MPAlc is useful for developing antibodies capable of specifically binding to MPA. The term "antibody" as used herein refers to polyclonal and monoclonal antibodies and related antigen recognition units, including fragments and derivatives of immunoglobulin molecules. One method of producing antibodies is to administer the immunogen, generally combined with an adjuvant such as Freund's, in a series of injections to a host animal for the purpose of inducing an immunologic response. Such methods are well known to those skilled in the art. Methods for producing monoclonal antibodies were first described by Kohler and Milstein (Nature, Vol 256, pp 495–497, 1975; incorporated herein in its entirety) and have been modified several times since the appearance of that publication. For hybridoma technology, the reader is directed generally to U.S. Pat. Nos. 4,491,632, 4,472,500, and 4,444,887, and Methods in Enzymology, 73B:3 (1981); each is incorporated herein in entirety. Since the particular method is not critical, any proven method can be used to produce a polyclonal or monoclonal antibody using the immunogens described herein.

Antibodies obtained using any of the aforementioned techniques are screened, selected or purified not only on the basis of specific binding to MMF, MPA and/or AcMPAG, but also for low cross-reactivity with potential interfering substances and/or inactive metabolites such as 7-O-MPAG. "Cross reactivity" is determined in a quantitative immunoassay by establishing a standard curve using known dilutions of MPA. The standard curve is then used to calculate the apparent concentration of the interfering substance present in various known amounts in samples assayed under substantially similar conditions. The percent (%) cross-reactivity is the measured concentration divided by the tested concentration multiplied by 100%.

In another embodiment of the invention, an MPAlc-carb-MEA adduct is prepared and used to form conjugates with other molecules or solid matrices that are useful as labeling compounds in immunoassays. Such conjugates include, but are not limited to, enzymes, enzyme donors, enzymes fragments, biotin, fluorescent molecules, radioisotopes, metal sols, latex particles, membranes, polymer surfaces, and the like. Use of a linker at the hydroxyl oxygen at position 1' of MPAlc for the purposes of conjugation with the labeling molecule or particles is generally preferred. Linkers can be of different lengths and different structures, as is known in the art. The reader is referred generally to Hermanson, G. T., "Bioconjugate Techniques", Academic Press: New York, 1996; and "Chemistry of Protein Conjugation and Crosslinking" by S. S. Wong, CRC Press, 1993, incorporated herein. In a preferred embodiment, a maleimidoethylamine adduct of MPAlc or MPA is formed, as described in Examples 4 or 6, respectively, and conjugates comprising the adduct and enzyme donor fragment are made as described in Examples 5 and 7.

The present invention also anticipates use of antibodies prepared from MPAlc-containing immunogens, as well as other conjugates prepared from MPAlc, as reagents for performing immunoassays for the quantitative detection of MPA. In testing for drugs, immunoassays, particularly competitive binding immunoassays, have enjoyed increasing popularity. In competitive binding immunoassays, an analyte, for example a target drug, in a specimen competes with a labeled reagent, or analyte analog, or a detectable tracer, for limited number of receptor binding sites on antibodies capable of specifically binding the analyte and/or analyte analog. Enzymes, including peroxidase, phosphatase, and β-galactosidase, and fluorescent molecules or particles are commonly used as labeling substances, and radioisotopes remain in use as labels. The amount of target analyte in a specimen determines how much labeled analyte or analyte analog becomes bound to the antibodies specific for the target analyte.

A preferred form of immunoassay is cloned enzyme donor immunoassay or CEDIA® (trademark of Roche Diagnostics), based upon the re-association of enzymatically inactive polypeptide fragments of β-galactosidase. In particular, β-galactosidase enzyme donor polypeptide fragment combines with a β-galactosidase enzyme acceptor fragment to form active β-galactosidase enzyme. The active enzyme complex is capable of transforming a substrate into a product that is differentially detectable. Usually, the product is a different color from the substrate and is quantified using spectrophotometric methods. Conjugating a hapten or other small analyte or analyte analog to the enzyme donor fragment at certain sites does not affect the ability to form active enzyme by the complementation reaction and does not affect the rate of enzymatic activity when in the presence of a substrate for β-galactosidase. However, when the enzyme donor-hapten conjugate is bound by the anti-analyte antibody, for example, when little or no analyte is present in a specimen being tested, the complementation reaction is inhibited, reducing the amount of active enzyme present in the reaction mixture. Hence, the enzyme-catalyzed reaction rate is decreased under such conditions. In contrast, when the specimen tested contains significant concentrations of a target analyte, it competes with the enzyme donor-hapten for binding sites on the anti-analyte antibody, thereby increasing the amount of active enzyme formed by complementation reaction. Therefore, the enzyme-catalyzed reaction rate is directly proportional to the concentration of target analyte present in the specimen tested.

A preferred β-galactosidase enzyme donor is ED28, a polypeptide containing residues 6–45 of β-galactosidase, with cysteines at postions 1 and 46 (relative to the numbering of the original β-galactosidase fragment). The maleimide adducts described in Examples 4 and 6 represent typical linker groups for conjugation to an enzyme donor.

Preferred substrates for use in immunoassays utilizing β-galactosidase include those described in U.S. Pat. Nos. 5,032,503; 5,254,677; 5,444,161; and 5,514,560, incorporated herein in entirety. Chlorophenol-red-β-D-galactopyranoside is an exemplary substrate.

The invention is demonstrated further by the following illustrative examples.

EXAMPLE 1

Preparation of Mycophenolic Alcohol

To a solution of mycophenolic acid (0.32 g) and triethylamine (0.28 mL) in tetrahydrofuran (THF) (5.0 mL) at −5° C., was added 0.692 ml of 27.7% ethyl chloroformate in THF and the mixture was stirred for about 30 minutes. Triethylamine hydrochloride was removed by filtration and the filtrate was added drop wise to NaBH$_4$ (0.19 g) in H2O (2 mL) at 10–15° C. The reaction mixture was stirred at room temperature for 18 hr, acidified with 3N HCl and extracted with ethyl acetate. The ethyl acetate extract was washed with water, dried over anhydrous magnesium sulfate (MgSO$_4$) and evaporated under reduced pressure. The residue was heated in 3N NaOH (3 mL) at 90° C. for 0.5 hr and acidified with 3N HCl. The reaction mixture was extracted with ethyl acetate, washed according to standard procedures with aqueous sodium bicarbonate and deionized water, and dried over anhydrous MgSO$_4$. The solvent was removed under reduced pressure to give 235 mg of mycophenolic alcohol (MPAlc) as a white crystalline solid, with a chemical structure as shown:

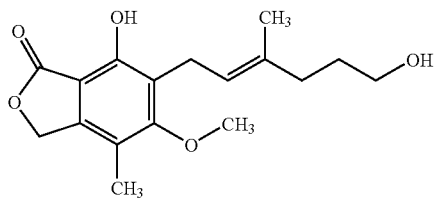

EXAMPLE 2

Preparation of MPAlc-carb-BSA Immunogen

To a stirred solution of MPAlc (36 mg, 0.117 mmol) in 1 ml of acetonitrile and pyridine (300 mg) was added disuccinimidyl carbonate (DSC) as a solid, in a portion-wise manner (10 mg per portion), and the reaction was monitored by thin layer chromatography (silica gel, methanol: chloroform, 10:90) until no starting material was left. The resulting N-hydroxysuccinimidyl carbonate ester (MPAlc-carb-NHS) has a chemical structure:

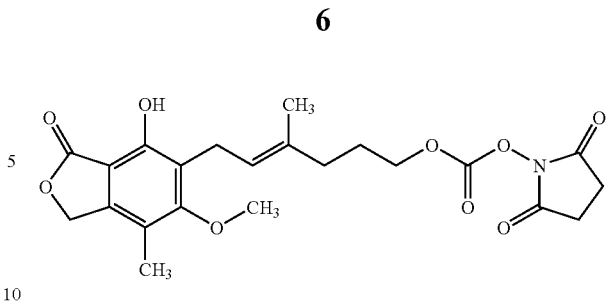

The MPAlc-carb-NHS ester is further reacted with a substance having immunogenic properties, such as bovine serum albumin (BSA), keyhole limpet hemocyanin (KLH), ocular lens proteins, ovalbumin, lipoproteins, and the like, or any antigenic fragment thereof, to produce an immunogen.

For example, to a solution of BSA (150 mg) in 0.1 M PBS, pH 8.0 (7 ml) and acetonitrile (1 ml) was added the above-described MPAlc-carb-NHS ester solution. The reaction mixture was stirred at 4° C. overnight and was purified by dialyzing against PBS-20% DMF, PBS two times using 2 L for each dialysis, for a minimum of 7 hours to give approximately 155 mg of MPAlc-carb-BSA immunogen, as shown:

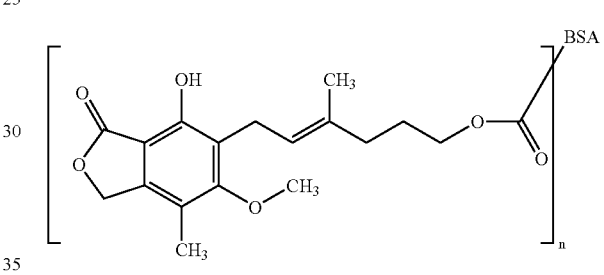

wherein n≧1 and preferably, in a range of 1 to 35. Other immunogenic proteins typically have different capacities for conjugating with haptens. For example, if KLH is used instead of BSA, the range for n is from 1 to about 500.

EXAMPLE 3

Preparation of Antibodies Using MPAlc-carb-BSA Immunogen

In a particular embodiment of the invention, the BSA-containing immunogen of Example 2 was administered to goats in a series of injections as is routine in the art. Alternatively, other mammals are suitable for antibody production. Screening of anti-serum samples taken from the immunized goats was performed to assess antibody titer and to evaluate the ability of antibodies in the samples to bind to enzyme-donor conjugate, as described in Examples 5 and 7, and to inhibit enzyme complementation with an enzyme-acceptor fragment. The selected anti-sera were further screened to determine whether free MPA modulates or competes with the enzyme-donor conjugate for the antibody using standard CEDIA protocols as cited above and incorporated herein. For the purposes of the present invention, a pool of anti-sera capable of specifically binding MPA without significant cross-reactivity (less than 5%; more preferably, <1%) to other immunosuppressants or to pharmacologically inactive MPA metabolites was prepared.

Alternatively, anti-sera, or supernatants in the case of monoclonal antibody production, may be tested for the production of antibodies by any number of methods well known to those skilled in the art, including, but not limited to ELISA or other standard immunoassays. For monoclonal antibody production, clones showing desired sensitivity and specificity are selected for further propagation. A supply of monoclonal antibody from the selected clone is then purified from a volume of culture supernatant or from ascites fluid of suitably prepared host animals injected with cells from the clone, as is routine in the art. Anti-sera, supernatants and/or ascites may be used unprocessed or, preferably, purified by biochemical means such as ammonium sulfate precipitation, gel filtration chromatography, or ion exchange chromatography, etc. The antibodies produced are suitable for a variety of immunoassay formats.

EXAMPLE 4

Preparation of MPAlc-carb-MEA Adduct

To a stirred solution of MPAlc (18 mg, 0.059 mmol) in acetonitrile (1 ml) and pyridine 150 mg was added DSC as a solid, portion wise (10 mg per portion), and the reaction was monitored by thin layer chromatography (silica gel, methanol: chloroform, 10:90) until no starting material was left. Thirty (30) mg of maleimidoethylamine hydrochloride was added to the reaction mixture. The reaction mixture was adjusted to pH 8.5 with triethylamine and the solution was stirred at room temperature for 30 minutes. The reaction mixture was purified by HPLC to give approximately 9.5 mg of MPAlc-carb-MEA as a white solid with a chemical structure as shown:

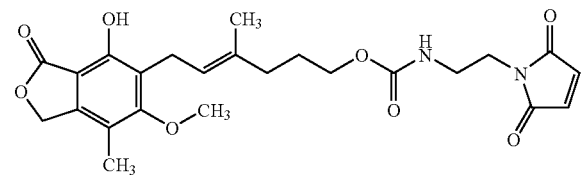

EXAMPLE 5

Preparation of MPAlc-carb-MEA Conjugates

Various conjugates can be made from the MPAlc-carb-MEA adduct including, but not limited to, conjugates comprising enzymes, enzyme fragments, fluorescence molecules, dyes, biotin, or particles such as metal sols, latex, and the like. In one embodiment, a conjugate for use in a CEDIA assay is prepared, in particular, a conjugate comprising an enzyme donor fragment. In general, the MPAlc-enzyme donor fragment conjugate has a general structure:

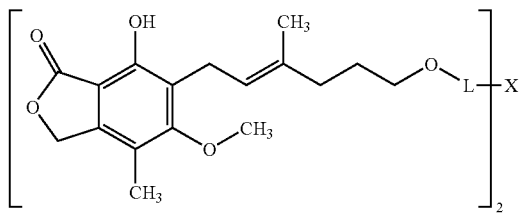

wherein L=linker and X=enzyme donor fragment.

For example, to a solution of 2.1 mg of enzyme donor fragment (ED28, as disclosed in U.S. Pat. No. 4,708,929 incorporated herein in entirety) in 1.4 ml of PBS, pH 7.0, was added a solution of 0.61 mg of MPAlc-carb-MEA in 0.5 ml of acetonitrile. The solution was mixed by vortexing for 5 seconds and kept at 4° C. for 45 minutes. MPAlc-carb-MEA-ED28 conjugate was purified by HPLC and quantitated spectrophotometrically.

EXAMPLE 6

Preparation of MPA-MEA Adduct

To a stirred solution of MPA (30 mg, 0.094 mmol) in dimethyl formamide (DMF) (3 ml) were added 1-ethyl-3-(3-dimethylaminopropyl)carbodiimide hydrochloride (EDAC) (45 mg, 0.235 mmol) and N-hydroxy-5-norbornene-2, 3-dicarboximide (42 mg, 0.235 mmol). The reaction mixture was stirred at room temperature for 3 hours and monitored by TLC (silica gel, methanol: chloroform, 5:95). Maleimidoethylamine hydrochloride (82.5 mg, 0.469 mmol) was added to the reaction mixture and the reaction mixture pH was adjusted to 8.5 with triethylamine (32 µl) and the solution was stirred at room temperature for 30 minutes. The reaction mixture was purified by HPLC to give approximately 10 mg of MPA-MEA as a white solid.

EXAMPLE 7

Preparation of MPA-MEA Conjugates

Various conjugates can be made from the MPA-MEA adduct including, but not limited to, conjugates comprising enzymes, enzyme fragments, fluorescence molecules, dyes, biotin, or particles such as metal sols, latex, and the like. For example, to a solution of 1 mg of ED28 enzyme in 1.12 ml of PBS, pH 7.0, was added a solution of 0.3 mg of MPA-MEA in 0.4 ml of acetonitrile. The solution was mixed by vortexing for 5 seconds and kept at 4° C. for 45 mins. The MPA-MEA-ED28 conjugate was purified by HPLC and quantitated spectrophotometrically.

EXAMPLE 8

CEDIA Assay for MPA

The CEDIA assay developed detects therapeutic ranges of MPA in serum or plasma, preferably a range of 0.2–10 µg per ml of serum or plasma, and is applicable for use with automated clinical chemistry analyzers, such as the Hitachi 911 or 917 or comparable analyzers. The assay is based upon the competition of MPA in the biological sample with MPA-MEA or MPAlc-carb-MEA conjugated to the inactive enzyme-donor (ED) fragment of beta-galactosidase, preferably ED28, for binding to the antibody raised against MPAlc, as described above. If MPA is present in the sample, it binds to the antibody, leaving the ED portion of the ED-containing conjugate free to restore enzyme activity upon association with enzyme acceptor (EA) fragments in the assay reaction mixture. The active enzyme is then capable of producing a quantifiable reaction product when exposed to appropriate substrate. If MPA is not present in the sample, the antibody binds to the ED-containing conjugate inhibiting association of the ED fragments with the EA fragments, thus inhibiting restoration of enzyme activity. The amount of reaction product and resultant absorbance change are proportional to the amount of MPA in the specimen.

Kits for performing CEDIA assays have been generally described in other patents cited herein. As an example, CEDIA kits for measuring MPA concentrations in fluid specimens, particularly plasma and serum samples, contain β-galactosidase enzyme acceptor (EA) reagent comprising EA lyophilized in a buffered salt solution, preferably at a concentration of about 0.118 grams of EA per liter of buffered salt solution prior to lyophilization. A preservative such as sodium azide is beneficial to increase the shelf life. Also included is an EA reconstitution buffer that includes antibodies capable of specifically binding MPA or, alternatively, antibodies capable of binding MPA plus MMF and/or AcMPAG. Preferred buffers include PIPES, MOPS, HEPES, TES or Tris.

The enzyme donor (ED) fragment conjugated to MPA or MPAlc is supplied in the kit as a separate reagent lyophilized along with the substrate. Chlorophenol-red-β-D-galactopyranoside at a concentration of about 10 nM (about 3.0 g/L) is a preferred substrate. Also, stabilizers, such as bovine serum albumin fragments, and preservatives, such as sodium azide, are beneficial in extending the shelf life. The ED reagent is reconstituted with ED reconstitution buffer comprising potassium phosphate, plus a non-ionic detergent (Tween 20, NP-40, etc.), and preservative. Additional components of the kit include instructions for performing the assay. Optionally, the kit may include calibrators, for example, at least one with no MPA (0 μg/ml MPA) and one in a higher concentration range (>5 μg/ml) and controls comprising known concentrations of the drugs. Calibrators and/or controls are included in kits or provided as separate components.

EXAMPLE 9

Within and Total Assay Precision (Reproducibility) of CEDIA MPA Assay

Within-run and total-run precision (reproducibility) studies were conducted using plasma specimens from: I) transplant patients taking MMF, ii) plasma spiked with MPA, and iii) controls. Three specimens from transplant patients taking MMF were assayed in a single run for precision. One pool of specimens from transplant patients (Patient Pool 2) and two spiked plasma samples (Patient Pools 1 and 3) were assayed in a total of twenty-one runs over eleven days using the modified protocol from NCCLS (EP5-A). Results are presented in Table 1.

TABLE 1

| Sample | n | Mean | Within-Run SD | Within-Run CV % | Total Run SD | Total Run CV % |
|---|---|---|---|---|---|---|
| Patient 1 | 21 | 1.0 | 0.04 | 4.3 | — | — |
| Patient 2 | 21 | 2.4 | 0.05 | 2.1 | | |
| Patient 3 | 21 | 6.1 | 0.10 | 1.6 | | |
| Pool 1 | 126 | 1.0 | 0.06 | 5.6 | 0.08 | 7.7 |
| Pool 2 | 126 | 2.4 | 0.07 | 2.8 | 0.09 | 4.0 |
| Pool 3 | 126 | 6.0 | 0.09 | 1.5 | 0.14 | 2.3 |
| Control 1 | 126 | 1.1 | 0.06 | 5.5 | 0.10 | 9.5 |
| Control 2 | 126 | 2.7 | 0.06 | 2.2 | 0.13 | 4.8 |
| Control 3 | 126 | 5.9 | 0.12 | 2.0 | 0.20 | 3.3 |

EXAMPLE 10

Linearity of CEDIA MPA Assay

To test linearity, a patient plasma sample containing a high concentration of MPA (9.8 μg/ml as determined by HPLC) was diluted using an MPA-free plasma sample to produce a series of samples across the dynamic range of the assay. Each sample was tested in replicates of five and the mean value was reported as measured or observed value. The percent recovery was determined by dividing the observed MPA concentration by the expected concentration. The expected concentrations were determined using the high concentration tested times a dilution factor. The results obtained are shown on Table 2.

TABLE 2

| % High Sample | Expected Value (μg/ml) | Observed Value (μg/ml) | Recovery (%) |
|---|---|---|---|
| 100 | 9.8 | 9.8 | 100 |
| 75 | 7.4 | 7.4 | 101 |
| 50 | 4.9 | 4.9 | 97 |
| 35 | 3.4 | 3.3 | 97 |
| 25 | 2.5 | 2.3 | 95 |
| 10 | 1.0 | 0.9 | 92 |
| 5 | 0.5 | 0.4 | 86 |
| 0 | 0.0 | 0.0 | N/A |

EXAMPLE 11

Recovery of MPA in CEDIA Assay

To assess recovery of MPA in the CEDIA assay, MPA was added to normal MPA-free plasma specimens and to transplant patient specimens containing MPA. Samples were tested in twenty-one replicates for normal plasma matrix (results shown on Table 3a) and five replicates for transplant sample matrix (results shown on Table 3b). Recovery was calculated by dividing the observed concentration of each sample by the expected concentration of added MPA plus MPA originally present in the samples.

TABLE 3a

| MPA-Free Plasma Samples | | |
|---|---|---|
| Expected Value (μg/ml) | Observed Value (μg/ml) | Recovery (%) |
| 0.0 | 0.0 | N/A |
| 0.5 | 0.5 | 100 |
| 1.0 | 0.9 | 90 |
| 2.5 | 2.5 | 100 |
| 3.5 | 3.2 | 91 |
| 7.0 | 6.5 | 93 |

TABLE 3b

| Transplant Patient Plasma Samples | | |
|---|---|---|
| Expected Value (μg/ml) Patient 1 | Observed Value (μg/ml) Patient 1 | % Recovery Patient 1 |
| 0.5 | 0.5 | N/A |
| 1.0 | 1.0 | 100 |
| 2.5 | 2.6 | 104 |
| Expected Value (μg/ml) Patient 2 | Observed Value (μg/ml) Patient 2 | % Recovery Patient 2 |
| 2.4 | 2.4 | N/A |
| 3.4 | 3.3 | 97 |
| 6.9 | 6.8 | 99 |

EXAMPLE 12

Specificity of CEDIA Assay for MPA

Different concentrations of the pro-drug, MMF, and MPA glucoronide metabolites, 7-O-MPAG (inactive metabolite) and AcMPAG (active metabolite), were added to MPA-free plasma for measuring cross-reactivity. The estimated cross-reactivity of each compound was calculated using the formula:

(measured concentration−control concentration)× 100% concentration tested

Results of studies performed using MMF and metabolites are shown on Table 4a.

TABLE 4a

| Compound | Concentration (µg/ml) | % Cross-Reactivity |
|---|---|---|
| Mycophenolate mofetil | 926 | 123 |
| 7-O-Glucuronide MPA | 1000 | 0.0 |
| Acyl glucuronide MPA | 10 | 192 |

Additionally, commonly co-prescribed and over-the-counter (OTC) drugs were tested in MPA-free plasma for cross-reactivity in the CEDIA MPA assay. The compounds listed on Table 4b showed no detectable cross-reactivity (0% cross-reactivity) at the indicated test concentrations.

TABLE 4b

| Other Drugs Tested: | Concentration tested, µg/ml |
|---|---|
| Acetaminophen | 100 |
| N-acetylprocainamide | 100 |
| Acyclovir | 100 |
| Amikacin | 100 |
| Amphotericin B | 100 |
| Ampicillin | 100 |
| Azathioprine | 100 |
| Carbamazepine | 100 |
| Chloramphenicol | 100 |
| Cimetidine | 100 |
| Ciprofloxacin | 100 |
| Cyclosporine | 10 |
| Digoxin | 10 |
| Digitoxin | 10 |
| Disopyramide | 100 |
| Erythromycin | 100 |
| Fluconazole | 100 |
| Flucytosine | 100 |
| Furosemide | 100 |
| Gancyclovir | 100 |
| Gentamicin | 100 |
| Hydrocortisone | 100 |
| Itraconazole | 100 |
| Kanamycin A | 100 |
| Kanamycin B | 100 |
| Ketoconazole | 100 |
| Lidocaine | 100 |
| Methylprednisolone | 100 |
| Morphine | 100 |
| Penicillin | 100 |
| Phenobarbital | 100 |
| Phenytoin | 100 |
| Prazosin | 100 |
| Prednisolone | 100 |
| Prednisone | 100 |
| Procainamide | 100 |
| Quinidine | 100 |
| Rifampicin | 60 |
| Sodium salicylate | 50 |
| Sirolimus | 0.3 |
| Spectinomycin | 100 |
| Streptomycin | 100 |

TABLE 4b-continued

| Other Drugs Tested: | Concentration tested, µg/ml |
|---|---|
| Tacrolimus | 0.3 |
| Theophylline | 100 |
| Tobramycin | 100 |
| Triamterene | 100 |
| Valproic Acid | 100 |
| Vancomycin | 100 |
| Verapamil | 100 |

EXAMPLE 13

Sensitivity of the CEDIA MPA Assay

The functional sensitivity, defined as the lowest drug concentration that gives a coefficient of variation (CV %) of $\leq 20\%$, is 0.3 µg/ml. Twenty-one MPA negative plasma specimens were tested for least detectable dose (LDD); the LDD is 0.2 µg/ml.

EXAMPLE 14

Method Comparison

Comparison between LC/MC (x) and the CEDIA MPA assay (y) was conducted using plasma and serum specimens from renal and heart transplant patients. Table 5 summaries the results obtained by EP Evaluator release 6.0.

TABLE 5

| | Deming's Regression | | |
|---|---|---|---|
| Sample | n | Slope | Intercept | r |
| Plasma | 183 | 1.129 | −0.124 | 0.9446 |
| | | (1.074–1.1184) | (−0.288–0.040) | |
| Serum | 98 | 1.074 | −0.158 | 0.9268 |
| | | (0.991–1.158) | (−0.415–0.099) | |
| Both | 281 | 1.110 | −0.138 | 0.9378 |
| | | (1.064–1.156) | (−0.277–0.000) | |

Although the present invention is described herein, the specification and examples are illustrative and not limiting. Other embodiments and modifications may suggest themselves to those skilled in the art without departing from the spirit and scope of the following claims.

What is claimed is:

1. An immunogen of the structure:

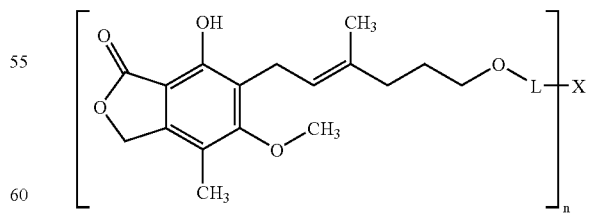

wherein L=a linker group, X=an antigenic carrier molecule and $n \geq 1$.

2. The immunogen of claim 1 wherein the antigenic carrier molecule comprises a protein, polypeptide, or poly (amino acid).

3. The immunogen of claim 1 wherein the antigenic carrier molecule is either keyhole limpet hemocyanin with n=1–500, or bovine serum albumin with n=1–35.

4. The immunogen of claim 1 wherein the linker group comprises a carbonyl group.

5. An antibody produced by the immunogen of claim 4, said immunogen containing either bovine serum albumin or keyhole limpet hemocyanin as antigenic carrier molecule, wherein said antibody is capable of binding to mycophenolic acid with a cross-reactivity of at least 90% and with a cross-reactivity of no more than 1% with 7-O-MPAG.

6. The antibody of claim 5 wherein said antibody is a polyclonal antibody or a monoclonal antibody.

7. The antibody of claim 5 wherein said antibody has a cross-reactivity of greater than 90% with AcMPAG.

8. A reagent for use in an immunoassay for mycophenolic acid having the structure:

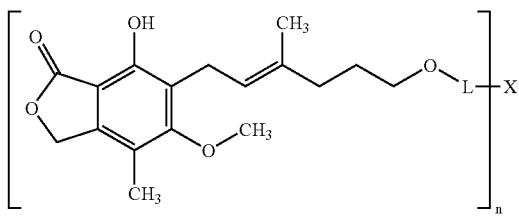

wherein L=a linker group, X=a detectable label or solid substrate and n≧1.

9. The reagent of claim 8 wherein X is a detectable label comprising an enzyme or enzyme fragment.

10. The reagent of claim 8 wherein X is a detectable label comprising an enzyme donor fragment capable of undergoing a complementation reaction with an enzyme acceptor fragment, said complementation reaction resulting in restoration of enzymatic activity.

11. The reagent of claim 8 wherein X is a detectable label comprising β-galactosidase enzyme donor designated ED28 and n=2.

12. A method of measuring the concentration of mycophenolic acid in a specimen suspected of containing mycophenolic acid comprising:
    (a) reacting the specimen with the antibody of claim 5 in the presence of a labeled reagent comprising mycophenolic acid, or mycophenolic alcohol, or a derivative thereof, conjugated to a detectable label; and
    (b) measuring the signal associated with the detectable label to determine the concentration of mycophenolic acid in the specimen.

13. The method of claim 12 wherein the detectable label comprises an enzyme donor fragment capable of undergoing a complementation reaction with an enzyme acceptor fragment that results in restoration of enzymatic activity.

14. A method of detecting mycophenolic acid in a specimen suspected of containing mycophenolic acid comprising:
    (a) reacting the specimen with the antibody of claim 5 in the presence of a labeled reagent comprising mycophenolic acid, or mycophenolic alcohol, or a derivative thereof, conjugated to a detectable label; and
    (b) detecting the detectable label as an indicator of the presence or absence of mycophenolic acid in the specimen.

15. The method of claim 14 wherein the detectable label comprises an enzyme donor fragment capable of undergoing a complementation reaction with an enzyme acceptor fragment that results in restoration of enzymatic activity.

* * * * *